(12) United States Patent
Roy (10) Patent No.: US 7,767,238 B2
(45) Date of Patent: Aug. 3, 2010

(54) BEVERAGE COMPOSITION AND METHOD OF PREVENTING DEGRADATION OF VITAMINS IN BEVERAGES

(75) Inventor: Glenn Roy, Beacon, NY (US)

(73) Assignee: PepsiCo, Inc., Purchase, NY (US)

( * ) Notice: Subject to any disclaimer, the term of this patent is extended or adjusted under 35 U.S.C. 154(b) by 1238 days.

(21) Appl. No.: 11/267,376

(22) Filed: Nov. 4, 2005

(65) Prior Publication Data

US 2007/0110851 A1 May 17, 2007

(51) Int. Cl.
*A23L 1/303* (2006.01)
*A23L 1/27* (2006.01)
(52) U.S. Cl. .............................. 426/72; 426/73; 426/590
(58) Field of Classification Search .................... 426/72, 426/73, 590
See application file for complete search history.

(56) References Cited

U.S. PATENT DOCUMENTS

| 6,811,804 | B2 | 11/2004 | Patel |
|---|---|---|---|
| 2003/0143311 | A1 | 7/2003 | Gillota |
| 2003/0215550 | A1* | 11/2003 | Higashimura et al. ........ 426/262 |
| 2005/0158424 | A1 | 7/2005 | Nakano |
| 2006/0051472 | A1* | 3/2006 | Koda et al. ................... 426/262 |

FOREIGN PATENT DOCUMENTS

| DE | 199 35 763 A1 | 2/2001 |
|---|---|---|
| EP | 0928565 A1 | 7/1999 |
| JP | 03272643 A | 12/1991 |
| JP | 07241181 A | 9/1995 |
| JP | 10-510523 | 10/1998 |
| JP | 2001-323263 | * 11/2001 |
| JP | 2001323263 | * 11/2001 |
| RU | 2 073 465 C1 | 2/1997 |
| WO | 2005068485 A | 7/2005 |

OTHER PUBLICATIONS

J.R. "The color of vitamin A." Science News, Jul. 17, 1999, p. 1.*
Official Action is related Japanese Patent Application No. 2006-298834, dated Aug. 4, 2009.

* cited by examiner

*Primary Examiner*—Helen F Pratt
(74) *Attorney, Agent, or Firm*—Banner & Witcoff, Ltd.

(57) ABSTRACT

A vitamin fortified composition comprising vitamin stabilizers which are $C_6$-$C_3$ phenylpropenoic carbonyl compounds to prevent the degradation of the vitamins is provided. In addition, a method of preventing the degradation of vitamins in a vitamin fortified composition is provided.

14 Claims, 7 Drawing Sheets

Rosmarinic Acid

Fig. 3(a)

Chlorogenic Acid

Fig. 3(b)

Cichoric Acid

Fig. 3(c)

Cinnamoyl Ester

Fig. 4(a)

Coumarin

Fig. 4(b)

Chalcone

Fig. 4(c)

Flavone

Fig. 4(d)

Chromone

Fig. 4(e)

Isoflavone

Fig. 4(f)

rhoifolin

Fig. 5(a)

rutin

Fig. 5(b)

BEVERAGE COMPOSITION AND METHOD OF PREVENTING DEGRADATION OF VITAMINS IN BEVERAGES

FIELD OF THE INVENTION

The present invention relates to a method of preventing vitamin degradation in vitamin-containing compositions and the resulting composition, which may be a beverage. More particularly, the inventive composition is directed to a vitamin-containing composition that contains Vitamin A, Vitamin D, Vitamin $B_{12}$, or mixtures thereof and a vitamin stabilizer.

BACKGROUND OF THE INVENTION

Vitamins are essential nutrients which serve many functions. Vitamin deficiency has been cited as a neglected public health problem. As a result, the food and beverage industry has created vitamin fortified compositions to increase the vitamin intake by consumers. However, from the time the vitamin-containing product leaves the production facility and reaches the consumer, the product may be exposed to air, light, acid, temperature, and other ingredient interactions. Unfortunately, exposure to any of the above elements results in vitamin degradation.

It has been found that light penetration, particularly fluorescent light, in polyethylene terephthalate (PET) and glass bottles can degrade Vitamin A such that claims of Vitamin A content at trade age do not meet the recommended dietary allowance (RDA). Even at significant levels of 3500 International Units (IU) of Vitamin A, current technologies in PET could not spare Vitamin A content to a 20% dietary reference intake (DRI) claim of 1000 IU. For example, a freshly prepared 3500 IU Vitamin A containing fruit juice in a 20 oz. PET bottle exposed to typical store fluorescent light (as found in in-store visi-coolers) for one week results in approximately 1000 IU of remaining Vitamin A content. The average trade age to a consumer purchase could be significantly longer in time.

Therefore, a need exists to prevent degradation of vitamins in vitamin-containing compositions, including Vitamin A, as a result of exposure to light, particularly fluorescent light (as found in in-store visi-coolers) when the composition is contained in a clear or substantially clear bottle, such as PET and glass bottles.

SUMMARY OF THE INVENTION

Figure 1A:
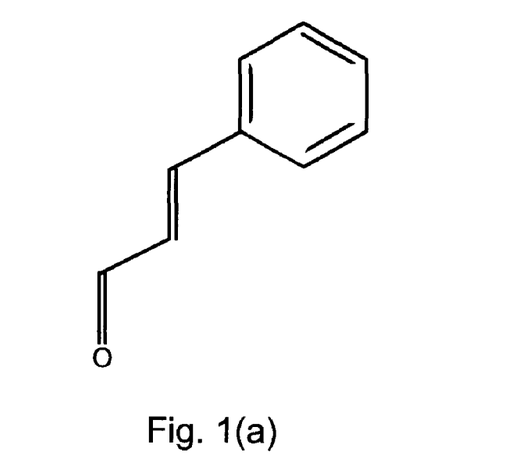
FIG. 1(a) shows the structure of a vitamin stabilizer according to an embodiment of the invention.
Figure 1B:
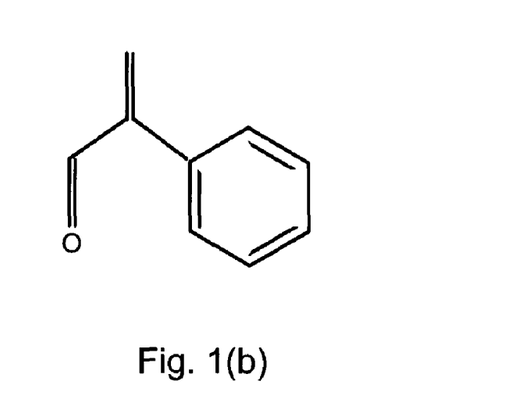
FIG. 1(b) shows the structure of a vitamin stabilizer according to another embodiment of the invention.
Figure 1C:
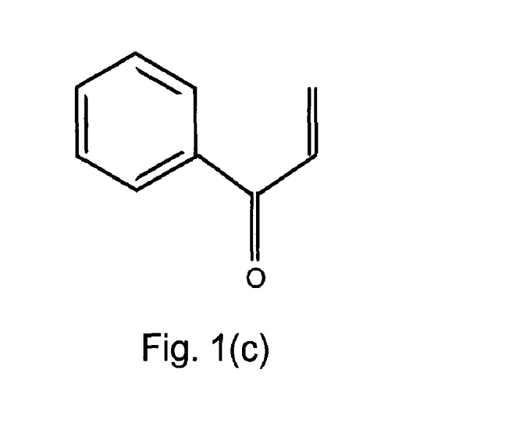
FIG. 1(c) shows the structure of a vitamin stabilizer according to a further embodiment of the invention.

In accordance with one aspect of the present invention, a vitamin-containing composition comprising a vitamin selected from Vitamin A, Vitamin D, Vitamin $B_{12}$, and mixtures thereof, and at least one vitamin stabilizer, is provided. Typically, the stabilizer will be present in an amount effective to provide at least some stabilization and provide protection from degradation of the vitamins present in the composition. The vitamin stabilizer stabilizes the vitamin or vitamins in the composition and prevents vitamin degradation from exposure to light and particularly to fluorescent light and comprises a vitamin stabilizer comprising a $C_6$-$C_3$ phenylpropenoic carbonyl structure represented by a formula selected from the structures of FIG. 1.

In accordance with another aspect of the present invention, a method for preventing or at least reducing vitamin degradation caused by light, and particularly by fluorescent light, in a vitamin-containing composition is provided. The method comprises adding at least one vitamin stabilizer comprising a $C_6$-$C_3$ phenylpropenoic carbonyl structure represented by any one of the formulas in FIG. 1 or mixtures thereof. Generally, at least one vitamin stabilizer is added in an amount effective to provide at least some vitamin stabilization to at least reduce the rate of vitamin degradation due to, for example, light exposure and particularly fluorescent light.

DETAILED DESCRIPTION OF THE INVENTION

Phenylpropenoic carbonyl compounds ($C_6$-$C_3$) have been found to prevent vitamin degradation in beverages. $C_6$-$C_3$ phenylpropenoic carbonyl compounds are ubiquitous in the family of secondary plant metabolites. Such compounds can be derived from a number of botanical substances or it can be manufactured synthetically. Many of these substances are currently approved for food and beverage use.

While not wishing to be bound by theory, it is believed that these compounds prevent degradation by acting as a vitamin stabilizer. The vitamin stabilizer is one of many substances known to be radical scavengers. Free radicals are believed to be the major reactive species in the process of light induced degradation of ingredients. When sufficient radical scavenger concentrations are maintained in a clear packaged beverage, light induced degradation of ingredients can be reduced to a certain level over the lifetime of a beverage on the shelf. It is believed that the vitamin stabilizers of the present invention scavenge free radicals generated in the beverage during fluorescent light degradation of Vitamin A. The fluorescent light exposure typically occurs when a beverage is stored in refrigerated visi-coolers installed in stores.

In accordance with one aspect of the present invention, a vitamin-containing composition is provided that comprises at least one vitamin and at least one vitamin stabilizer. Vitamins suitable for the present invention include, without limitation, Vitamin A and its palmitate, Vitamin D, Vitamin $B_{12}$ and mixtures thereof. Such vitamins are well known in the art and are readily commercially available.

The vitamin or vitamins can be present in the composition in amounts as desired. Typically, the vitamin is present in a vitamin-containing composition of the present invention in an amount sufficient to meet or exceed the recommended dietary allowance (RDA). However, the RDA are guidelines that are subject to revision from time to time; therefore, one of ordinary skill in the art will recognize that the amount of vitamin in the food composition can be adjusted to comply with the guidelines as they evolve or as they may exist at any point in time.

Figure 2A:
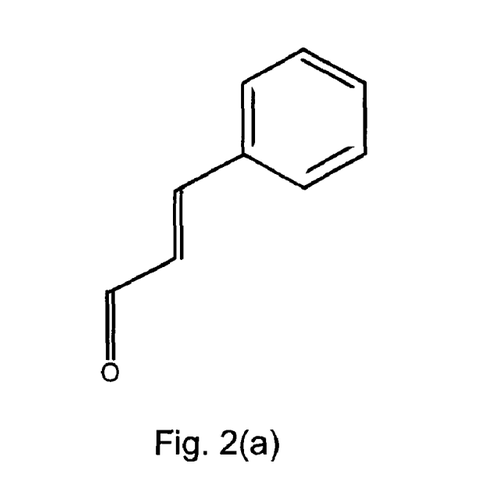
FIG. 2(a) shows a generic $C_6$-$C_3$ phenylpropenoic carbonyl structure represented by an isomeric formula, according to an embodiment of the invention.
Figure 2B:
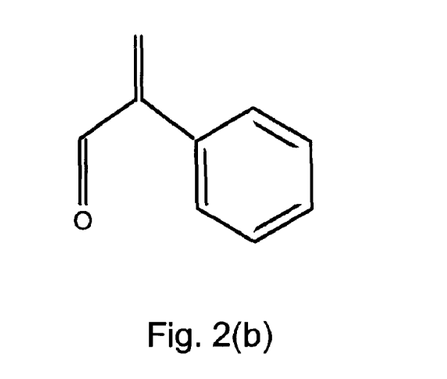
FIG. 2(b) shows a generic $C_6$-$C_3$ phenylpropenoic carbonyl structure represented by an isomeric formula, according to another embodiment of the invention.
Figure 2C:
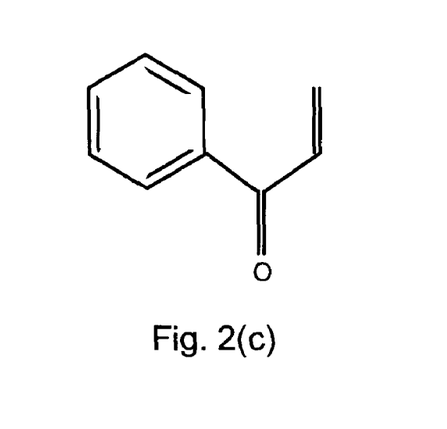
FIG. 2(c) shows a generic $C_6$-$C_3$ phenylpropenoic carbonyl structure represented by an isomeric formula, according to a further embodiment of the invention.
Figure 3A:
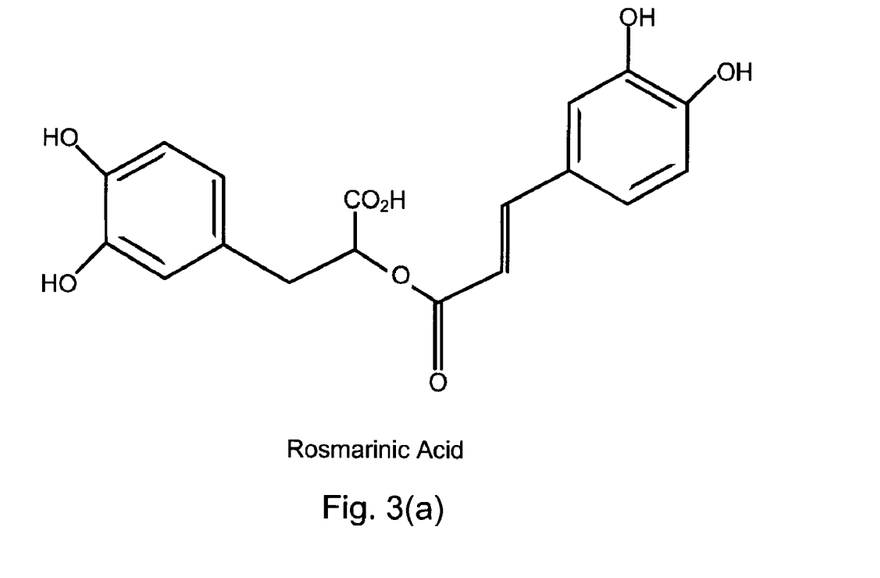
FIG. 3(a) shows the structure of rosmarinic acid.
Figure 3B:
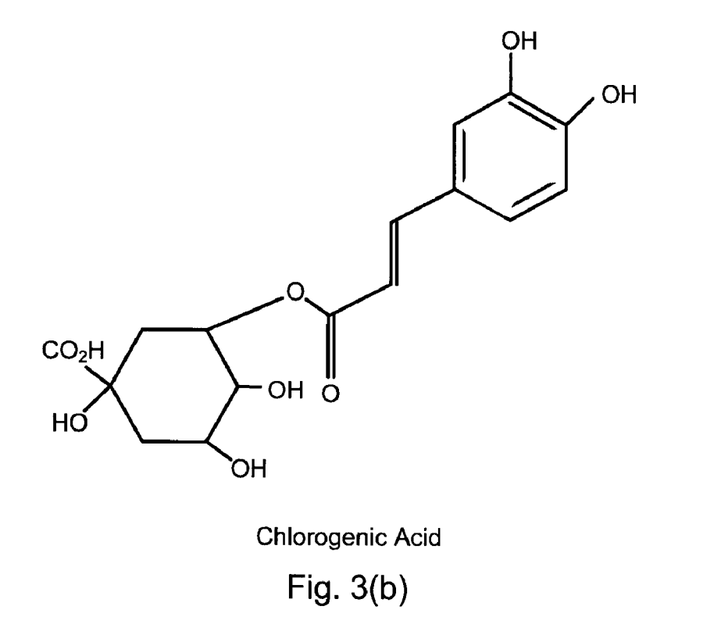
FIG. 3(b) shows the structure of chlorogenic acid.
Figure 3C:
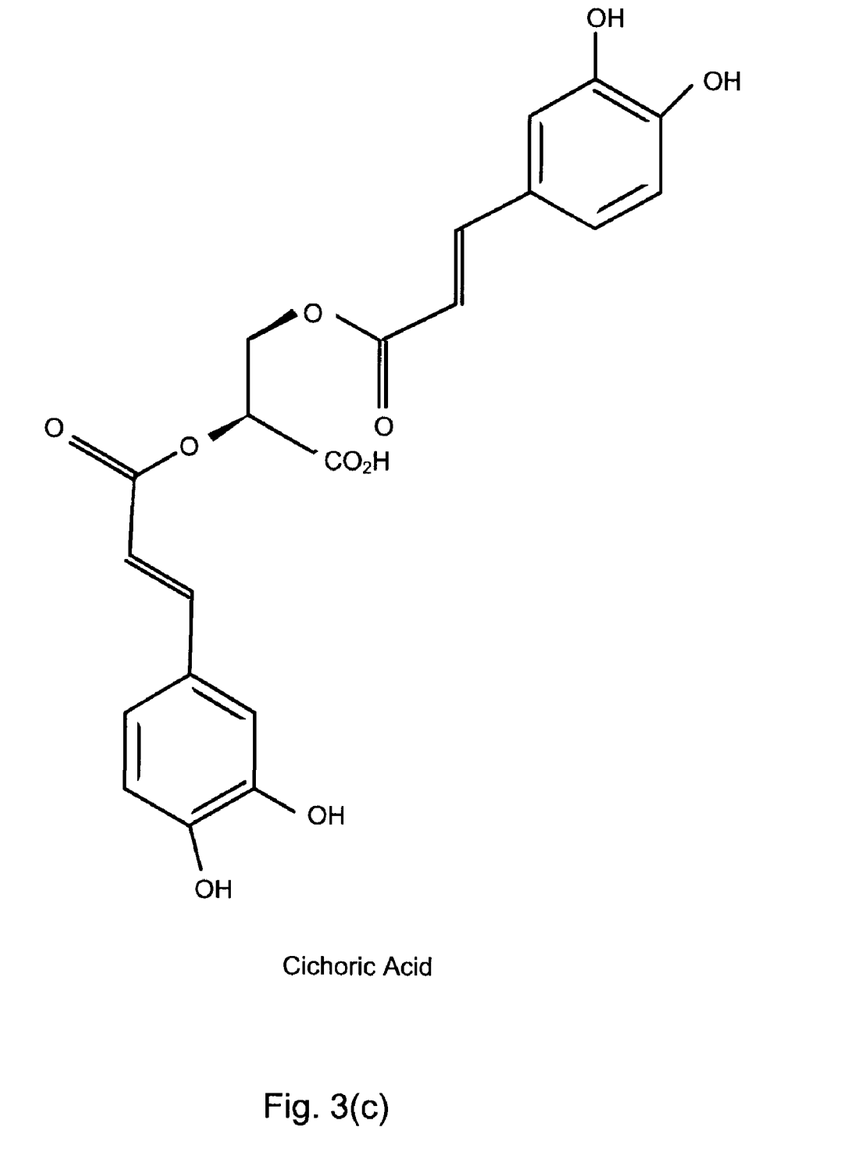
FIG. 3(c) shows the structure of cichoric acid.

The vitamin stabilizer of the present invention is, in its broadest sense, a $C_6$-$C_3$ phenylpropenoic carbonyl compound which contains both (i) unsaturation and (ii) oxidation at a carbon atom. The $C_6$-$C_3$ phenylpropenoic carbonyl compound can be either botanically derived or synthetically manufactured. The generic $C_6$-$C_3$ phenylpropenoic carbonyl structure can be represented by any of isomeric formulae (a), (b), and (c) of FIG. 2.

Any compound possessing such a structure alone or as part of a larger structure is suitable for use as a $C_6$-$C_3$ phenylpropenoic carbonyl compound, i.e., a botanically derived or synthetically manufactured vitamin stabilizer, of the present invention, provided that it provides at least some protection or reduction from vitamin degradation. The vitamin stabilizers may be commercially available, may be synthesized according to procedures known in the art or may be supplied by, derived from or isolated or extracted from known botanicals or extracts thereof. A representative extraction procedure includes the one disclosed by B. Buszewski, et al., J. Pharm. Biomed. Anal., vol. 11, no. 3, p. 211-215 (1993).

In accordance with one aspect of the present invention, $C_6$-$C_3$ phenylpropenoic carbonyl compounds suitable for use in the present invention include, without limitation, rosmarinic acid, chlorogenic acid, cichoric acid, caffeic acid, coumaric acid, cinnamic acid, ferulic acid, sinapic acid, caftaric acid, eichloric acid, echinacoside and combinations thereof. It is clear from the structures set forth in FIG. 3 that the generic structure FIG. 2(a) is present in materials such as rosmarinic acid, chlorogenic acid, and cichoric acid.

It is also clear from the structures of these substances that substitution of the generic $C_6$-$C_3$ phenylpropenoic carbonyl structure FIG. 2(a), and for that matter substitution of structures FIG. 2(b) and FIG. 2(c), so long as both unsaturation near and oxidation at a carbon atom remain, is intended. In fact, substitution is necessary to obtain a wide range of suitable vitamin stabilizers. Suitable substituents include, without limitation, hydroxyl, methoxyl, and others as usually found in plant metabolite phenols. Further, it can be readily appreciated that cichoric acid may well be a more effective vitamin stabilizer than some of the other listed acids, given the presence of two structures FIG. 2(a) therein. Generally, it is found that the addition of hydroxyl groups on the aryl rings enhances vitamin stabilization. Hence, vitamin stabilization ability of caffeic acid (2 hydroxyl groups)>ferulic acid>coumaric acid>cinnamic acid (no hydroxyl groups) is observed.

In certain preferred embodiments of the present invention, the above-listed $C_6$-$C_3$ phenylpropenoic carbonyl compound of the botanically derived vitamin stabilizer is provided via an extract of a botanical. Extracts suitable for use in the present invention include, without limitation, rosemary extract, green coffee bean extract, blueberry extract, rhododendron extract, sunflower kernel extract, chicory leaf extract, purple coneflower extract, lettuce extract and combinations thereof. More generally, extracts of botanicals in any of the labiatae, ericaceae or asteraceae families are suitable for use. As can be seen in Table 1 below, each of the above-noted extracts contains one or more $C_6$-$C_3$ phenylpropenoic carbonyl compounds which serve as a vitamin stabilizer.

TABLE 1

| common name | species | $C_6$–$C_3$ phenylpropenoic carbonyl compound(s) |
| --- | --- | --- |
| rosemary | Rosmarinus officinalis | rosmarinic acid |
| green coffee bean | Coffea Arabica | chlorogenic acid |
| blueberry | Vaccinium vulgaris | chlorogenic acid |
| rhododendron | Rhododendron caucasicum (Ungem) | chlorogenic acid |
| sunflower kernel | Helianthus annuus | chlorogenic acid |
| chicory leaves | Cichorium intybus | cichoric acid |
| purple coneflower | Echinacea angustifolia | echinacoside, cichoric acid, caftaric, eichloric acid |
| purple coneflower | Echinacea purpurea (Moench) | cichoric acid, chlorogenic acid, echinacoside |
| lettuce | Lactuca sativa | cichoric acid |

One of ordinary skill in the art will readily appreciate that the amount of a $C_6$-$C_3$ phenylpropenoic carbonyl compound present in a given extract will vary. Different species by nature may possess varying amounts of a $C_6$-$C_3$ phenylpropenoic carbonyl compound. The amount may also vary depending on the stage of development of a given botanical. As an illustration, Table 2 below shows the variation in chlorogenic acid and echinacoside content in the 'Magical Ruth' cultivar of Echinacea purpurea.

TABLE 2

Variations in the content of echinacoside and chlorogenic acid in flower heads of *Echinacea purpurea* cultivar 'Magical Ruth'*

| | Hydrophilic components (%) | |
| --- | --- | --- |
| Flower stage | Chlorogenic acid | Echinacoside |
| I (early) | 0.060 | 0.012 |
| II (medium) | 0.024 | 0.022 |
| III (mature) | 0.023 | 0.015 |
| IV (overblown) | 0.020 | 0.016 |

*results are obtained from 20 plants replicated three times; W. Letchamo, et al., "Cichoric Acid . . . in *Echinacea purpurea* as Influenced by Flower Developmental Stages", Perspectives on New Crops and New Uses, J. Janick, ed., ASHS Press, Alexandria, VA, pp. 494-498 (1999).

In addition, the cichoric acid content of 'Magical Ruth' varies from 4.67% at stage I to 1.42% at stage IV. Therefore, it would seem that early cultivation would provide the richest extract of desirable vitamin stabilizers.

Other $C_6$-$C_3$ phenylpropenoic carbonyl compounds suitable for use in the present invention include, without limitation, cinnamoyl esters, coumarins, chalcones, flavones, chromones, isoflavones, and combinations thereof. Many of these types of compounds can be derived from a group of known natural products called flavonoids, which are found in fruits, vegetables, nuts, seeds and flowers, as well as in teas and wines; flavonoids have demonstrated many biological and pharmacological activities such as anti-bacterial, anti-fungal, anti-viral, anti-oxidant, anti-inflammatory, anti-mutagenic and anti-allergic and inhibitory activities on several enzymes. As can be seen from structures of FIG. 4, each of cinnamoyl esters FIG. 4(a), coumarins FIG. 4(b), chalcones FIG. 4(c) and flavones FIG. 4(d) incorporates the generic $C_6$-$C_3$ structure FIG. 2(a), chromones FIG. 4(e) incorporate the generic $C_6$-$C_3$ structure FIG. 2(c) and isoflavones FIG. 4(f) incorporate the generic $C_6$-$C_3$ structure FIG. 2(b).

Figure 4A:
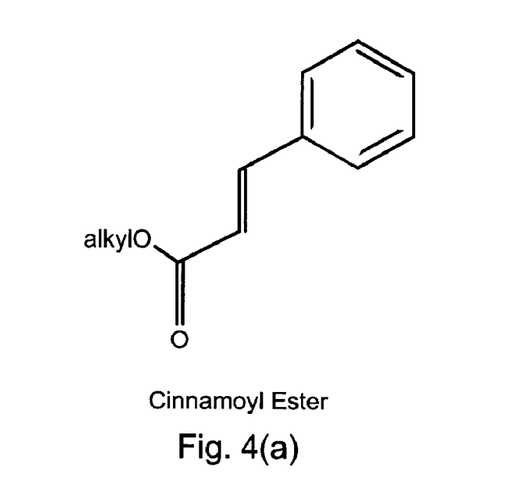
FIG. 4(a) shows the structure of cinnamoyl ester.

Cinnamoyl esters (flavors) suitable for use in the present invention include, without limitation, cinnamyl formate, cinnamyl acetate, ethyl cinnamate, cinnamyl propionate, cinnamyl alpha-toluate, cinnamyl 2-amino benzoate, cinnamyl anthranilate, cinnamyl benzoate, cinnamyl beta-phenyl acrylate, cinnamyl butyrate, cinnamyl cinnamate, cinnamyl isobutyrate, cinnamyl isovalerate, cinnamyl methyl ketone, cinnamyl ortho-amino benzoate, cinnamyl phenyl acetate, cinnamyl 3-phenyl propenoate and combinations thereof. It is clear that substitution on the generic structure FIG. 4(*a*), so long as both unsaturation near and oxidation at a carbon atom remain, is intended. In fact, substitution is necessary to obtain a wide range of suitable vitamin stabilizers. Suitable substituents for the generic structure FIG. 4(*a*) include, without limitation, any alkyl group including linear, non-linear, cyclic and acyclic alkyls, as well as unsubstituted and substituted alkyls.

Figure 4B:
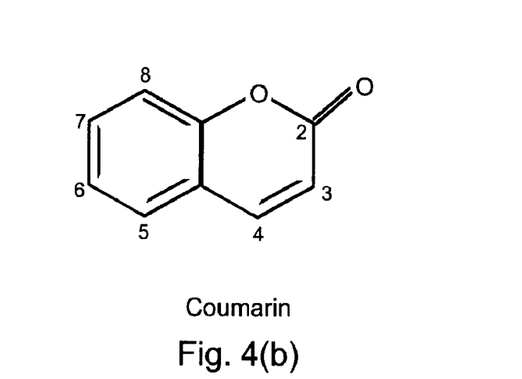
FIG. 4(b) shows the structure of coumarin.

Coumarins suitable for use in the present invention include, without limitation, coumarin, coumestrol, dalbergin, daphnetin, esculetin, citropten, noralbergin, umbelliferone, scopoletin, xanthotoxol, psoralen, bergapten, fraxetin and combinations thereof. It is clear that substitution on the generic structure FIG. 4(*b*), so long as both unsaturation near and oxidation at a carbon atom remain, is intended. In fact, substitution is necessary to obtain a wide range of suitable vitamin stabilizers. Suitable substituents for the generic structure FIG. 4(*b*) include, without limitation, OH, OCH$_3$, C$_6$H$_4$O$_2$, Ph and CH$_2$=CHO. Table 3 below sets forth the substituents present for the above-listed coumarin compounds suitable for use in the present invention.

TABLE 3

Exemplary coumarins with substituent positions.

coumarin FIG. 4(*b*)

| name | \multicolumn{6}{c}{substituent position} |
| | 3 | 4 | 5 | 6 | 7 | 8 |
| --- | --- | --- | --- | --- | --- | --- |
| coumestrol | C$_6$H$_4$O$_2$ | | | | OH | |
| dalbergin | | | | OH | | OCH$_3$ |
| daphnetin | | | | | OH | OH |
| esculetin | | | | | OH | |
| citropten | | | | OCH$_3$ | OCH$_3$ | |
| noralbergin | | Ph | | OH | | OH |
| umbelliferone | | | | | OH | |
| scopoletin | | | | OCH$_3$ | OH | |
| xanthotoxol | | | | CH$_2$=CHO | | OH |
| psoralen | | | | CH$_2$=CHO | | |
| bergapten | | | | OCH$_3$ | CH$_2$=CHO | |
| fraxetin | | | | | OCH$_3$ | OH |

Notes:
Ph = phenyl
blank box = H

Figure 4C:
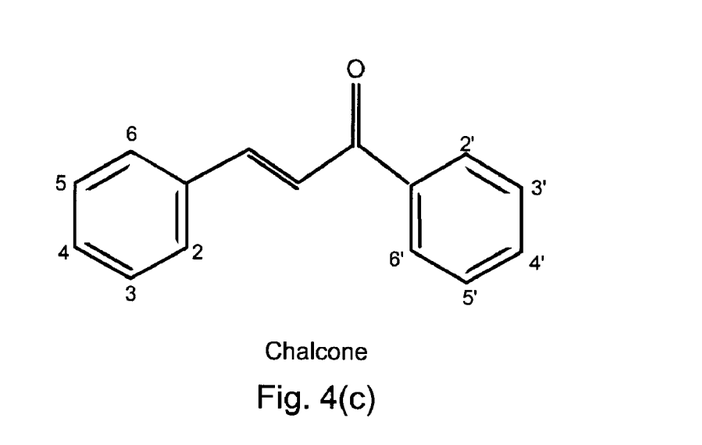
FIG. 4(c) shows the structure of chalcone.

Chalcones suitable for use in the present invention include, without limitation, chalcone, polyhydroxychalcones, butein, phloridzin, echinatin, marein, isoliquiritigenin, phloretin and combinations thereof. It is clear that substitution on the generic structure FIG. 4(*c*), so long as both unsaturation near and oxidation at a carbon atom remain, is intended. In fact, substitution is necessary to obtain a wide range of suitable vitamin stabilizers. Suitable substituents for the generic structure FIG. 4(*c*) include, without limitation, OH, OCH$_3$ and OGlc. Table 4 below sets forth the substituents present for the above-listed chalcone compounds suitable for use in the present invention.

TABLE 4

Exemplary chalcones with substituent positions.

chalcone FIG. 4(*c*)

| name | \multicolumn{7}{c}{substituent position} |
| | 2 | 3 | 4 | 2' | 3' | 4' | 6' |
| --- | --- | --- | --- | --- | --- | --- | --- |
| butein | | OH | OH | OH | | OH | |
| phloridzin | | | OH | OGlc | | OH | OH |
| echinatin | OCH$_3$ | | | | OH | OH | |
| marein | | OH | OH | OH | OH | OGlc | |
| isoliquiritigenin | OH | | OH | | | OH | |
| phloretin | | | OH | OH | | OH | OH |

Notes:
Glc = glucose
blank box = H

Flavones suitable for use in the present invention include, without limitation, rhoifolin, diosmin, apiin, apigenin, myricetin, kaempferol, luteolin, morin, neodiosmin, quercetin, rutin, balcalein, cupressuflavone, datiscetin, diosmetin, fisetin, galangin, gossypetin, geraldol, hinokiflavone, scutellarein, flavonol, primuletin, pratol, robinetin, quercetagetin, (OH)$_4$ flavone, tangeritin, sinensetin, fortunelin, kampferide, chrysoeriol, isorhamnetin, vitexin and combinations thereof.

Flavones are primarily bitter, e.g., quercetin, and insoluble. However, at the use levels of the vitamin stabilizers, the normally associated bitter tastes are not perceived in the utilized beverage matrices due to the phenomenon of mixture suppression of bitterness by the formulated sweetness and sourness. The maximally preferred use levels of all vitamin stabilizers are governed by their solubility in the desired beverage matrices as determined by routine experimentation.

Figure 4D:
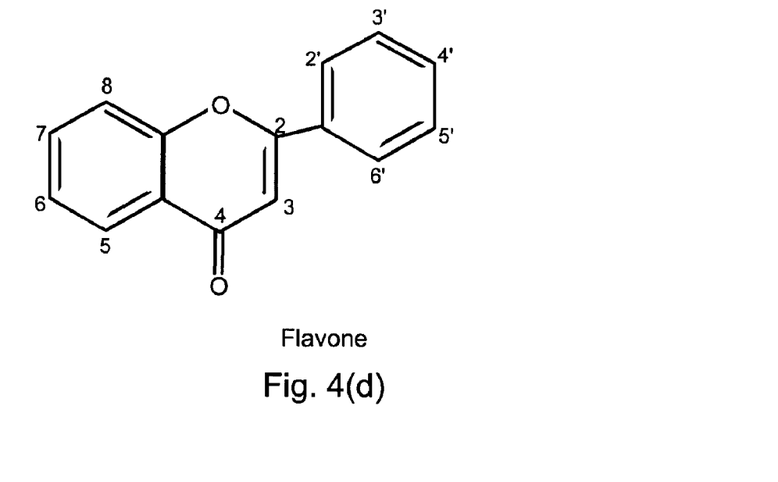
FIG. 4(d) shows the structure of flavone.
Figure 5A:
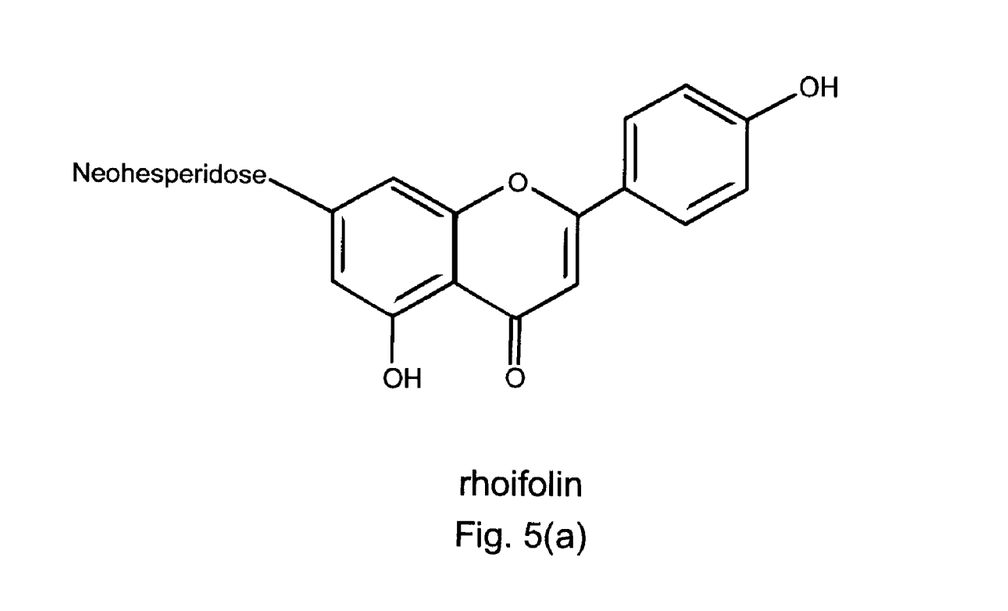
FIG. 5(a) shows the structure of rhoifolin.
Figure 5B:
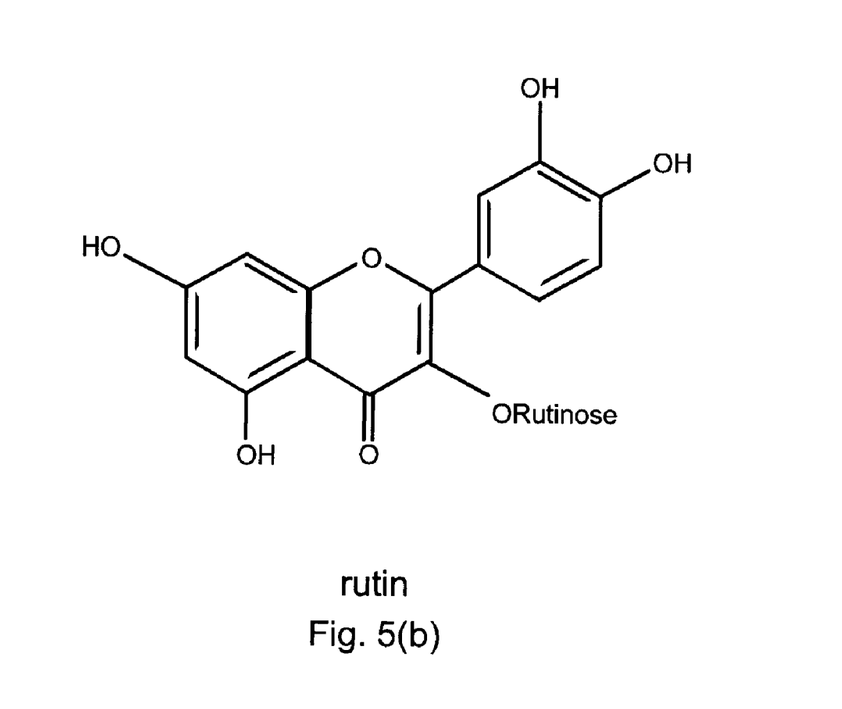
FIG. 5(b) shows the structure of rutin.

It is clear from the structures set forth in FIG. 5 that generic structure FIG. 4(*d*) is present in materials such as rhoifolin and rutin.

It is also clear from the structures of these flavones that substitution on the generic structure FIG. 4(*d*), so long as both unsaturation near and oxidation at a carbon atom remain, is intended. In fact, substitution is necessary to obtain a wide range of suitable vitamin stabilizers. Suitable substituents include, without limitation, OH, ORut, OApioGlc, ONeoHesp, dimer, OCH$_3$ and OGlc. Table 5 below sets forth the substituents present for the above-listed flavone compounds suitable for use in the present invention.

TABLE 5

Figure 4E:
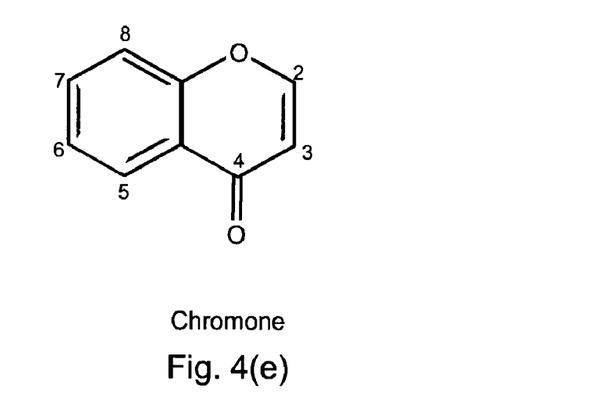
FIG. 4(e) shows the structure of chromone.

Exemplary flavone with substituent positions.

flavone FIG. 4(d)

| Name | 3 | 5 | 6 | 7 | 8 | 2' | 3' | 4' | 5' |
|---|---|---|---|---|---|---|---|---|---|
| rhoifolin |  | OH |  | ONeoHesp |  |  |  | OH |  |
| diosmin |  | OH |  | ORut |  |  | OH | OCH₃ |  |
| Apiin |  |  |  | OApioGlc |  |  |  | OH |  |
| apigenin | OH | OH |  | OH |  |  |  | OH |  |
| myricetin | OH | OH |  | OH |  |  | OH | OH | OH |
| kaempferol | OH | OH |  | OH |  |  |  | OH |  |
| luteolin |  | OH |  | OH |  |  | OH | OH |  |
| morin | OH | OH |  | OH |  | OH |  | OH |  |
| neodiosmin |  | OH |  | ONeoHesp |  |  | OH | OCH₃ |  |
| quercitin | OH | OH |  | OH |  |  | OH | OH |  |
| rutin | ORut | OH |  | OH |  |  | OH | OH |  |
| balcalein |  | OH | OH | OH |  |  |  |  |  |
| cupressuflavone |  | OH |  | OH | dimer |  |  | OH |  |
| datiscetin | OH | OH |  | OH |  | OH |  |  |  |
| diosmetin |  | OH |  | OH |  |  | OH | OCH₃ |  |
| fisetin | OH |  |  | OH |  |  | OH | OH |  |
| galangin | OH | OH |  | OH |  |  |  |  |  |
| gossypetin | OH | OH |  | OH | OH |  | OH | OH |  |
| geraldol | OH |  |  | OH |  |  | OH | OCH₃ |  |
| hinokiflavone |  | OH | OGlc | OH |  |  | OH | OH |  |
| scutellarein |  | OH | OH | OH |  |  |  | OH |  |
| flavonol | OH |  |  |  |  |  |  |  |  |
| primuletin |  | OH |  |  |  |  |  |  |  |
| pratol |  |  |  | OH |  |  |  |  |  |
| robinetin | OH |  |  | OH |  |  | OH | OH | OH |
| quercetagetin | OH | OH | OH | OH |  |  | OH | OH |  |
| (OH)₄flavone |  |  |  | OH | OH |  | OH | OH |  |
| tangeritin |  | OCH₃ | OCH₃ | OCH₃ | OCH₃ |  |  | OCH₃ |  |
| sinensetin |  | OCH₃ | OCH₃ | OCH₃ |  |  | OCH₃ | OCH₃ |  |
| fortunelin |  | OH |  | OH |  |  |  | OCH₃ |  |
| kampferide | OH | OH |  | OH |  |  |  | OCH₃ |  |
| chrysoeriol | OH | OH |  | OH |  |  | OCH₃ | OH |  |
| isorhamnetin | OH | OH |  | OH |  |  | OH | OCH₃ |  |
| vitexin |  | OH |  | OH | Glc |  |  | OH |  |

Notes:
Rut = rutinose;
NeoHesp = neohesperidose;
ApioGlc = apiose-glucose;
Glc = glucose
blank box = H Chromones such as chromone are suitable for use in the present invention. It is clear that substitution on the generic structure FIG. 4(e), so long as both unsaturation near and oxidation at a carbon atom as in FIG. 2(c) remain, is intended. In fact, substitution is necessary to obtain a wide range of suitable vitamin stabilizers. Suitable substituents for the generic structure FIG. 4(e) include, without limitation, OH, OCH₃, OGlc, and the like.

Isoflavones suitable for use in the present invention include, without limitation, daidzin, daidzein, biochamin A, prunetin, genistin, glycitein, glycitin, genistein, 6,7,4'-tri(OH)isoflavone, 7,3', 4'-tri(OH)isoflavone and combinations thereof. It is clear that substitution on the generic structure FIG. 4(f), so long as both unsaturation near and oxidation at a carbon atom as in FIG. 2(b) remain, is intended. In fact, substitution is necessary to obtain a wide range of suitable vitamin stabilizers. Suitable substituents for the generic structure FIG. 4(f) include, without limitation, OH, OCH₃ and OGlc. Table 6 below sets forth the substituents present for the above-listed isoflavone compounds suitable for use in the present invention.

TABLE 6

Figure 4F:
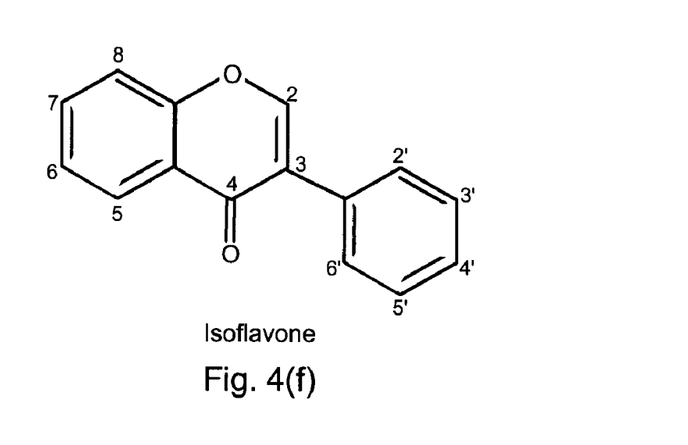
FIG. 4(f) shows the structure of isoflavone.

Exemplary isoflavone with substituent positions.

isoflavone FIG. 4(f)

| name | substituent position | | | | |
|---|---|---|---|---|---|
| | 5 | 6 | 7 | 3' | 4' |
| daidzin | | | OGlc | | OH |
| daidzein | | | OH | | OCH$_3$ |
| biochamin A | OH | | OH | | OH |
| prunetin | OH | | OCH$_3$ | | OH |
| genistin | OH | | OGlc | OCH$_3$ | OH |
| glycitein | | OCH$_3$ | OH | OH | OH |
| glycitin | | OCH$_3$ | OGlc | | OH |
| genistein | OH | | OH | | OH |
| 6,7,4'-tri(OH)isoflavone | | OH | OH | | OH |
| 7,3',4'-tri(OH)isoflavone | | | OH | OH | OH |

Notes:
Glc = glucose
blank box = H

In certain preferred embodiments of the present invention, the above-noted $C_6$-$C_3$ phenylpropenoic carbonyl compounds having any of generic structures FIG. 4(a)-(f) can be supplied via an extract of a botanical. Extracts suitable for use in the present invention include, without limitation, horse chestnut, dandelion, eucalyptus, red stringybark, saw palmetto, honeysuckle, hawthorn, noni fruit, red clover, orange, grapefruit, citrumelo, attani, pummelo, sour, orange, lemelo, Natsudaidai orange, buckwheat, chamomile and combinations thereof. As can be seen in Table 7 below, each of the above-noted extracts contains one or more $C_6$-$C_3$ phenylpropenoic carbonyl compounds which serve as a botanically derived vitamin stabilizer.

TABLE 7

| common name | species | $C_6$-$C_3$ phenylpropenoic carbonyl compound(s) |
|---|---|---|
| horse chestnut | Aesculus hippocastanum | rutin, esculetin |
| dandelion | Taraxacum | esculetin |
| eucalyptus | Eucalyptus oblique | rutin, esculetin |
| red stringybark | E. macrohyncha | rutin, esculetin |
| saw palmetto (sabal or shrub palmetto) | Serenoa repens in Family Arecaceae | isoquercitrin, kaempferol-3-O-glucosides, rhoifolin |
| honeysuckle | Lonicera japonica | luteolin, quercetin, astragalin, isoquercitrin, diosmetin 7-O-glucoside, rhoifolin, lonicerin |
| hawthorn | Crataegus specie | vitexin |
| noni fruit | Morinda citrifolia | morin, rutin |
| red clover | Trifolium pretense | isoflavones |
| orange | Citrus sinensis | rutin, flavones, chalcones, coumarins |
| grapefruit | | rhoifolin, isorhoifolin |
| citrumelo | P. trifoliate × C. paradise | rutin, isorhoifolin, rhoifolin |
| attani, pummelo, sour, orange, lemelo, Natsudaidai orange | | rhoifolin |

TABLE 7-continued

| common name | species | $C_6$-$C_3$ phenylpropenoic carbonyl compound(s) |
|---|---|---|
| buckwheat | Fagopyrum specie | rutin |
| chamomile | Anthemis specie | apigenin-7-glucoside |

As noted above with regard to the botanicals of Table 7, one of ordinary skill in the art will readily appreciate that the amount of a $C_6$-$C_3$ phenylpropenoic carbonyl compound present in a given extract will vary. Different species by nature may possess varying amounts of a $C_6$-$C_3$ phenylpropenoic carbonyl compound. The amount may also vary depending on the stage of development of a given botanical or the portion of the botanical from which the extraction is performed. For example, for many of the citrus fruits, higher concentrations of flavones and flavonols occur in the leaves than in the flavedo, albedo and juice vesicles.

Typically, any of the above-noted vitamin stabilizers (generic structures FIG. 2(a)-(c) and FIG. 4(a)-(f) is present in a vitamin-containing composition of the present invention in an amount sufficient to provide an amount of stabilizer in a beverage ranging from about 10 ppm to about 500 ppm, preferably from about 50 ppm to about 300 ppm, and more preferably from about 100 ppm to about 200 ppm. When the vitamin stabilizer is supplied via an extract of a botanical, the extract is present in a vitamin-containing composition of the present invention in an amount sufficient to provide an amount of stabilizer in a beverage in the same amounts noted above. It is important to note that extracts may have varying amounts of stabilizer contained therein. For example, an extract may contain 5% active ingredient or stabilizer; accordingly, the use of 500 ppm of the extract would result in the use of 25 ppm of the stabilizer.

A second aspect of the present invention is directed to a method of preventing vitamin degradation in a vitamin-containing beverage comprising adding to said beverage a vitamin stabilizing amount of a vitamin stabilizer.

Beverages include, without limitation, carbonated soft drinks, fountain beverages, frozen ready-to-drink beverages, coffee beverages, tea beverages, powdered soft drinks, as well as liquid concentrates, flavored waters, vitamin-enhanced waters, fruit juice and fruit juice flavored drinks, sport drinks, dairy products and alcoholic products. The beverage may be carbonated or noncarbonated. The beverage may be hot-filled.

The vitamin-containing beverage may be fortified by virtue of the presence of one or more of the above-noted vitamins. Additionally, the vitamin stabilizer is also the same as described above with respect to the first aspect of the present invention. The vitamin-containing composition may be included at any stage of beverage manufacture, i.e., syrup, concentrate, finished beverage.

As noted above, a "vitamin stabilizing amount" refers to an amount sufficient to substantially lessen or prevent the degradation of vitamins in a vitamin-containing beverage. Typically, a vitamin stabilizer is added to a vitamin-containing beverage in an amount ranging from about 10 ppm to about 500 ppm, preferably from about 50 ppm to about 300 ppm, and more preferably from about 100 ppm to about 200 ppm. When the vitamin stabilizer is supplied via an extract of a botanical, the extract is present in a vitamin-containing food composition of the present invention in an amount sufficient to provide an amount of stabilizer in a beverage in the same amounts noted above.

Optionally, the method of preventing degradation of vitamins in a vitamin-containing beverage according to the present invention further comprises adding to said beverage a non-aryl enoic carbonyl compound selected from sorbic acid, aconitic acid, abscisic acid, fumaric acid, maleic acid, or any combination thereof. When present, a non-aryl enoic carbonyl compound is typically added to a beverage in an amount ranging from about 10 ppm to about 200 ppm, and preferably from about 25 ppm to about 100 ppm.

A third aspect of the present invention is directed to a stable vitamin-containing beverage comprising a vitamin and a vitamin stabilizing amount of a vitamin stabilizer. The stable vitamin-containing beverage of the third aspect of the present invention may optionally contain a non-aryl enoic carbonyl compound selected from sorbic acid, aconitic acid, abscisic acid, fumaric acid, maleic acid, or any combination thereof. The amounts of each of the vitamin, the vitamin stabilizer and the non-aryl enoic carbonyl compound are as described above with respect to the first and second aspects of the invention.

EXAMPLES

TABLE 8

| | IU of Vitamin A Palmitate | | | |
| --- | --- | --- | --- | --- |
| | Example 1 | Example 2 | Example 3 | Example 4 |
| Dark | 2300 | 1870 | 3215 | 1500 |
| Light | 576 | 548 | 737 | 960 |
| 33 ppm Rutin | 878 | — | — | — |
| 66 ppm Rutin | 1215 | — | 1824 | — |
| 100 ppm Rutin | — | 856 | — | — |
| 100 ppm SanMelin AO-3000 | — | 987 | — | 1261 |
| 33 ppm Blueberry leaves extract | 1400 | — | — | — |

Example 1

Clear L/L CSD with Vitamin C and EDTA in Clear Glass

A clear lemon-lime (L/L) carbonated soft drink (CSD) with Vitamin C and ethylene-diaminetetraacetic acid (EDTA) was prepared. Seven samples of the carbonated soft drink were prepared each containing 2500 IU of Vitamin A Palmitate which can be obtained from Roche and the amount of rutin, SanMelin or blueberry leaves extract indicated in Table 8. All samples were packaged in clear glass containers. The Dark and Light samples were each free of rutin, SanMelin or blueberry leaves extract. The Dark sample was shielded from light. All the other samples, including the Light sample were exposed to typical store fluorescent light. The values in the table were all measured at one week.

Example 2

Clear L/L CSD with Vitamin C and EDTA in Clear Glass

Example 2 differed from Example 1 in that the starting amount of Vitamin A Palmitate was 2000 IU.

Example 3

Pink Lemonade 5% Juice Non-Carbonated in PET Bottle

A non-carbonated pink lemonade beverage composed of 5% juice was prepared. Seven samples like the ones in Examples 1 and 2 were prepared except that the starting amount of Vitamin A Palmitate was 3500 IU and the samples were packaged in PET containers.

Example 4

High Acid Milk Product in Clear Glass, Retorted

A high acid milk product was prepared. Seven samples like the ones in Example 2 were prepared each containing 2000 IU of Vitamin A Palmitate and retorted.

While the invention has been described with respect to certain preferred embodiments, as will be appreciated by those skilled in the art, it is to be understood that the invention is capable of numerous changes, modifications and rearrangements and such changes, modifications and rearrangements are intended to be covered by the following claims.

The invention claimed is:

1. A vitamin-containing composition comprising a vitamin selected from the group consisting of Vitamin A, Vitamin D, Vitamin $B_{12}$, and mixtures thereof, and a vitamin stabilizer consisting essentially of one or more flavones, the one or more flavones comprising a $C_6$-$C_3$ phenylpropenoic carbonyl structure, and wherein the vitamin stabilizer lessens the degradation of the vitamin upon exposure to fluorescent light as compared to the same vitamin-containing composition without the vitamin stabilizer.

2. The vitamin-containing composition according to claim 1, wherein the Vitamin A is Vitamin A Palmitate.

3. The vitamin-containing composition according to claim 1, wherein the vitamin stabilizer is present in an amount sufficient to provide an amount of vitamin stabilizer in a beverage ranging from about 10 ppm to about 500 ppm.

4. The vitamin-containing composition according to claim 3, wherein the vitamin stabilizer is present in an amount sufficient to provide an amount of vitamin stabilizer in a beverage ranging from about 50 ppm to about 300 ppm.

5. The vitamin-containing composition according to claim 4, wherein the vitamin stabilizer is present in an amount sufficient to provide an amount of vitamin stabilizer in a beverage ranging from about 100 ppm to about 200 ppm.

6. The vitamin-containing composition according to claim 1, wherein the vitamin stabilizer is botanically derived.

7. The vitamin-containing composition according to claim 6, wherein the botanically derived vitamin stabilizer is supplied by an extract of a botanical.

8. The vitamin-containing composition according to claim 7, wherein the extract is selected from the group consisting of horse chestnut extract, eucalyptus extract, stringybark extract, saw palmetto extract, honeysuckle extract, hawthorn extract, noni fruit extract, orange extract, buckwheat extract, chamomile extract and mixtures thereof.

9. The vitamin-containing composition according to claim 1, wherein the vitamin stabilizer is synthetically derived.

10. The vitamin-containing composition according to claim 1, wherein the flavone is selected from the group consisting of rhoifolin, diosmin, apiin, apigenin, myricetin, kaempferol, luteolin, morin, neodiosmin, quercetin, rutin, balcalein, cupressuflavone, datiscetin, diosmetin, fisetin, galangin, gossypetin, geraldol, hinokiflavone, scutellarein, flavonol, primuletin, pratol, robinetin, quercetagetin, $(OH)_4$ flavone, tangeritin, sinensetin, fortunelin, kampferide, chryoeriol, isorhamnetin, vitexin and mixtures thereof.

11. The vitamin-containing composition according to claim 10, wherein the rutin is an enzymatically modified isoquercitrin.

12. The vitamin-containing composition according to claim 1 further comprising a non-aryl enoic carbonyl compound selected from the group consisting of sorbic acid, aconitic acid, abscisic acid, fumaric acid, maleic acid and mixtures thereof.

13. A method of preventing degradation of vitamins in a vitamin-containing beverage comprising:

adding a vitamin stabilizing compound consisting essentially of one or more flavones, wherein said stabilizing compound comprises a $C_6$-$C_3$ phenylpropenoic carbonyl structure, and wherein the vitamin stabilizing compound lessens the degradation of the vitamin upon exposure to fluorescent light as compared to the same vitamin-containing beverage without the vitamin stabilizing compound.

14. A stable, vitamin-containing beverage comprising a vitamin selected from the group consisting of Vitamin A, Vitamin D, Vitamin $B_{12}$ and mixtures thereof, and a vitamin stabilizer consisting essentially of one or more flavones comprising a $C_6$-$C_3$ phenylpropenoic carbonyl structure, and wherein the vitamin stabilizer lessens the degradation of the vitamin upon exposure to fluorescent light as compared to the same vitamin-containing beverage without the vitamin stabilizer.

* * * * *